United States Patent
Bateman

(10) Patent No.: US 6,652,496 B2
(45) Date of Patent: Nov. 25, 2003

(54) OSTOMY BAGS

(75) Inventor: Timothy Bateman, Dymchurch (GB)

(73) Assignee: Mentor Medical Limited (GB)

( * ) Notice: Subject to any disclaimer, the term of this patent is extended or adjusted under 35 U.S.C. 154(b) by 0 days.

(21) Appl. No.: 09/932,116

(22) Filed: Aug. 20, 2001

(65) Prior Publication Data

US 2002/0026162 A1 Feb. 28, 2002

(30) Foreign Application Priority Data

Aug. 25, 2000 (GB) ............................................. 0020901

(51) Int. Cl.⁷ ................................................... A61F 5/44
(52) U.S. Cl. ....................................... 604/342; 604/339
(58) Field of Search ............................. 604/336–339, 604/341, 344, 332–335, 340, 342–343, 345

(56) References Cited

U.S. PATENT DOCUMENTS

| 4,917,689 A | 4/1990 | Coombes |
| 5,013,307 A | 5/1991 | Broida |
| 5,380,309 A | 1/1995 | Keyes et al. |
| 5,496,296 A * | 3/1996 | Holmberg ................... 604/336 |
| 5,865,819 A | 2/1999 | Cisko, Jr. et al. |
| 2001/0020156 A1 * | 9/2001 | Whiteside ................... 604/342 |

FOREIGN PATENT DOCUMENTS

| EP | 0 388 924 | 9/1990 | |
| GB | 2017501 | 10/1979 | |
| GB | 2157567 | 10/1985 | |
| GB | 2257056 | 1/1993 | |
| GB | 2273052 | 6/1994 | |
| GB | 2 277 031 A * | 10/1994 | ........... A61F/5/443 |
| WO | WO 00/30576 | 6/2000 | |

* cited by examiner

*Primary Examiner*—Weilun Lo
*Assistant Examiner*—Linh Truong
(74) *Attorney, Agent, or Firm*—Fish & Richardson P.C., P.A.

(57) ABSTRACT

An wc-disposable ostomy bag has a pouch of alkali-disposable material and an adhesive flange in two parts. One part is an inner ring permanently bonded with the pouch around its opening. The other part forms the major part of the flange and is an outer ring attached with the pouch by a temporary, manually-separable bond. The outer ring can be disposed of separately from the pouch and inner ring, which are placed in a wc to which an alkali has been added. The small size of the inner ring enables it to be flushed away.

13 Claims, 1 Drawing Sheet

OSTOMY BAGS

BACKGROUND OF THE INVENTION

This invention relates to ostomy bags.

Attempts have been made recently to develop ostomy bags which can be disposed of by flushing in a wc, to avoid the need to make special disposal arrangements, which can be inconvenient, embarrassing and unhygenic.

WC-disposable bags have been proposed in the literature, the bags having an outer water-soluble or dispersible layer and an inner water-resistant layer. The outer layer provides mechanical support for the inner layer so that, when the bag is dropped into turbulent water in a wc pan, the outer layer is quickly broken up. The inner layer prevents the contents of the bag attacking the outer layer in use but, once the outer layer is broken up on disposal, the inner layer does not have sufficient mechanical strength in itself to cause blockage on flushing the wc. An example of such a bag is described in GB 2083762B. A wc-disposable bag is sold by SIMS Portex Limited, England under the name Symphony (Symphony is a Registered Trade Mark of SIMS Portex Limited).

Although such bags can be used satisfactorily, the user has to take special precautions to ensure that the outside of the bag does not become wet, because the outer layer would be damaged by contact with water. This can be especially inconvenient with bags which are worn long-term, for two or more days, such as is usually the case with ileostomy bags. The use of such bags can make washing difficult and prevents the user swimming.

An alternative form of bag is described in EP 0142950A, which is made of 3-hydroxybutyrate film, either in a laminate with a water-soluble film as an outer layer, or entirely from 3-hydroxybutyrate. Such a material remains intact when in contact with water or body waste, but is broken up if the pH is raised to about 12. The bag described is disposed of by adding a base material to the contents of the bag so as to raise the pH of the contents to at least 12 so that it breaks up when agitated in a wc pan.

A further alkali-disposable bag is described in GB 2195919B. The walls of this bag have a central layer of polyvinyl alcohol, an inner layer of a blend of polyvinylidene chloride acrylonitrile copolymer with carboxylated acrylic copolymer, and an outer layer of two or more coatings of carboxylated acrylic acid. This bag can be disposed of in a wc by adding an alkali to the water in the pan.

Another alkali-disposable bag is described in GB 2257056. This bag has an outer layer substantially entirely of alkali-soluble/water-insoluble carboxylated acrylic polymer forming a major part of the thickness of the material and a thinner, inner layer of alkali-resistant polyvinylidene chloride bonded directly to one side of the first layer. GB 2324761 describes an alkali-disposable bag with a non-woven outer layer.

Previous bags have a flange around their inlet opening supporting an adhesive material by which the bag is attached to the skin of the patient. In order to provide the desired security of attachment, the flange is thicker and stiffer than the walls of the bag. Although the flange can be made such that it can be flushed away in a wc, it can take longer to flush away and the perceived bulk of the flange can make users think that it will not flush away, or that it will create a blockage.

BRIEF SUMMARY OF THE INVENTION

It is an object of the present invention to provide an alternative ostomy bag.

According to one aspect of the present invention there is provided an ostomy bag comprising a flexible pouch and a flange by which the bag is attached to the patient, the pouch having a forward wall and a rear wall facing the patient, the rear wall having an opening therein through which waste material from the patient can enter the pouch, the flange comprising an inner ring and an outer ring, both rings having an adhesive surface for attachment to the patient, and one of the rings being attached with the rear wall of the pouch by a permanent bond and the other ring is attached with the pouch by a temporary bond such that the other ring can be removed from the pouch for disposal separately from the pouch.

The other ring is preferably the outer ring and the outer part of the outer ring may be unattached with the pouch. The other ring is preferably attached with the rear wall. The outer ring may be of a double-sided pressure-sensitive adhesive material, the forward surface of the outer ring having a non-adhesive backing sheet attached with it. The inner and outer rings may be of the same material or have adhesive surfaces with different properties. The pouch is preferably wc disposable and may be alkali disposable.

According to another aspect of the present invention there is provided a method of disposing of an ostomy bag of the kind comprising a flexible pouch and a flange by which the bag is attached to the patient, the pouch having a forward wall and a rear wall facing the patient, the rear wall having an opening therein through which waste material from the patient can enter the pouch, the method comprising separating an outer part of the flange from an inner part of the flange, disposing of the outer part of the flange, sealing the bag at the remaining inner part of the flange and disposing of the bag in a wc.

The method may include the step of adding an alkali to the wc, allowing the alkali to break down the pouch and subsequently flushing away the pouch and inner part of the flange.

An ostomy bag according to the present invention will now be described, by way of example, with reference to the accompanying drawing.

DETAILED DESCRIPTION OF THE PREFERRED EMBODIMENT

Figure 1:
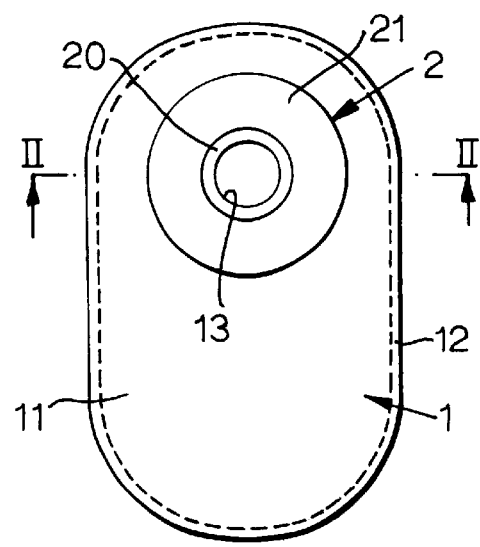
FIG. 1 is a view of the rear side of the bag.
Figure 2:
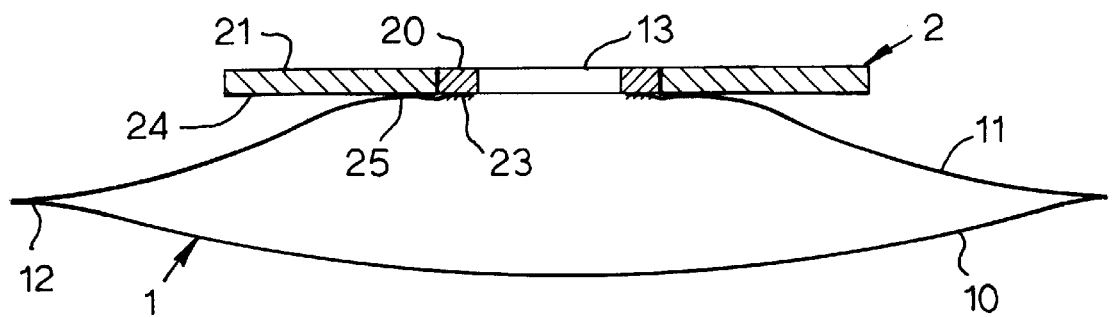
FIG. 2 is a sectional side elevation view of the bag along the line II—II of FIG. 1 to an enlarged scale.

The bag comprises a pouch 1 and a flange 2, a part of which is separable from the pouch after use.

The pouch 1 has a forward wall 10, facing away from the patient, and a rear wall 11, facing towards the patient and joined with the forward wall around its edge by a peripheral weld 12. The walls 10 and 11 are formed of a conventional alkali-disposable material, such as described in GB 2324761. Centrally towards its upper end, the pouch 1 has a circular opening 13 formed in the rear wall 11 through which waste material from the patient enters the pouch. The pouch may include other conventional features, such as a filter, but is otherwise made entirely of a flexible wc disposable material.

The flange 2 comprises an inner ring 20 and an outer ring 21, which extends concentrically around the inner ring and abuts or is closely spaced from the outer edge of the inner ring. The inner ring 20, or minor part, is relatively narrow radially compared with the outer ring 21, or major part, and has a smaller bulk. Both rings 20 and 21 are made of a conventional double-sided, skin-compatible, pressure-sensitive adhesive and are protected on their rear surface, before use, by a removable release sheet (not shown). The inner ring 20 is attached to the outer surface of the rear wall 11 of the pouch 1 around the opening 13 by a permanent bond 23, such as a continuous weld. The forward surface of the outer ring 21 facing away from the patient has a non-adhesive backing sheet 24 attached permanently to it. The outer ring 21 is also attached to the rear wall 11 of the pouch 1 but only by means of a manually-separable temporary bond 25, such as an interrupted weld or by tack joins. The bond 25 is located close to the inner edge of the outer ring 21, that is, close to the inner ring 20, so that the outer part of the outer ring is unattached to the pouch 1 and can flex away from it. The adhesive of the inner and outer rings 20 and 21 may of different kinds: the adhesive on the inner ring being softer and suited particularly to forming an effective gas and liquid seal around the stoma; the adhesive on the outer ring being selected to form a secure attachment to the skin.

In use, the user removes the release sheet from the flange 2 and applies the flange to the skin around the stoma in the usual way. When the bag is to be removed, the user peels the flange 2 away from the skin. He then grips the outer ring 21 and pulls it away from the pouch 1, so as to rupture the temporary bond 25 and separate the outer ring from the pouch. The outer ring 21 is then wrapped and disposed of in a waste container. The outer ring 21 will not normally be soiled because it is protected by the inner ring 20. The user then folds the bag across the opening 13, so that the inner ring 20 seals on itself or on another part of the bag, and drops it into the pan of a wc into which an alkali has been added. The pouch 1 is quickly broken up by the action of the alkali enabling it to be flushed away. Because the inner ring 20 has only a relatively small bulk, this can also be flushed away easily.

The present invention enables a large part of the flange of a bag to be removed before disposal in a wc. The invention could be modified in various ways. For example, the outer ring could be attached to the inner ring rather than directly to the pouch. The outer ring could be permanently attached with the pouch and the inner ring be removable and of greater bulk, although this would mean that the non-flushable portion could be more soiled.

What I claim is:

1. An ostomy bag comprising: a flexible pouch, said pouch having a forward wall and a rear wall, said rear wall positioned to face a patient and having an opening therein through which waste material from the patient can enter said pouch; and a flange by which the bag is attached to the patient, wherein said flange comprises an inner ring and an outer ring, wherein both said rings have an adhesive surface for attachment with the patient, and wherein one of said rings is attached with said rear wall of said pouch by a permanent bond and the other of said rings is attached with said pouch by a temporary bond such that said other ring can be removed from said pouch for disposal separately from said pouch.

2. An ostomy bag according to claim 1, wherein said other ring is said outer ring.

3. An ostomy bag according to claim 2, wherein said outer ring has an outer part unattached with said pouch.

4. An ostomy bag according to claim 1, wherein said other ring is attached with said rear wall.

5. An ostomy bag according to claim 1, wherein said outer ring is of a double-sided pressure-sensitive adhesive material, and wherein a forward surface of said outer ring has a non-adhesive backing sheet attached with it.

6. An ostomy bag according to claim 1, wherein said inner and outer rings are the same material.

7. An ostomy bag according to claim 1, wherein said inner and outer rings have adhesive surfaces with different properties.

8. An ostomy bag according to claim 1, wherein said pouch is wc disposable.

9. An ostomy bag according to claim 1, wherein said pouch dissolves in the presence of an alkali solution.

10. An ostomy bag comprising: a flexible pouch, said pouch having a forward wall and a rear wall, said rear wall positioned to face a patient and having an opening therein through which waste material from the patient can enter said pouch, wherein said flange comprises an inner ring and an outer ring, wherein both said rings have an adhesive surface for attachment to the patient, wherein said inner ring is attached with said rear wall of said pouch by a permanent bond, wherein said outer ring is attached with said pouch by a manually-separable bond such that said outer ring can be removed from said pouch, and wherein said pouch and inner ring can be flushed away in a wc so that they can be disposed of separately from said outer ring.

11. A method of disposing of an ostomy bag comprising a flexible pouch and a flange by which the bag is attached to a patient, said flange having an outer part and an inner part, same material said pouch having a forward wall and a rear wall, said rear wall positioned to face a patient and having an opening therein through which waste material from the patient can enter said pouch, wherein the method comprises (a) separating said inner and outer parts of said flange, (b) disposing of said outer part, and (c) disposing of the bag in a wc.

12. A method according to claim 11 including the step of adding an alkali to the wc, allowing said alkali to break down said pouch.

13. A method according to claim 11, further including the step of sealing the bag such that said inner part seals on itself or on another part of the bag.

* * * * *

UNITED STATES PATENT AND TRADEMARK OFFICE
CERTIFICATE OF CORRECTION

PATENT NO. : 6,652,496 B2
DATED : November 25, 2003
INVENTOR(S) : Timothy Bateman It is certified that error appears in the above-identified patent and that said Letters Patent is hereby corrected as shown below:

<u>Column 4,</u>
Line 41, please delete "same material".

Signed and Sealed this

Fourteenth Day of December, 2004

JON W. DUDAS
*Director of the United States Patent and Trademark Office*